(12) United States Patent
Morehead et al.

(10) Patent No.: US 8,800,628 B2
(45) Date of Patent: Aug. 12, 2014

(54) SELF-PROPELLED AIRSHIP HULL REPAIR SYSTEM

(75) Inventors: John Morehead, Santa Clarita, CA (US); Nicholas Piini, Palmdale, CA (US); Kyle Hofstatter, Santa Clarita, CA (US); Eric Younge, Hermosa Beach, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 388 days.

(21) Appl. No.: 13/479,182

(22) Filed: May 23, 2012

(65) Prior Publication Data

US 2013/0312895 A1 Nov. 28, 2013

(51) Int. Cl.
| | | |
|---|---|---|
| *B32B 41/00* | (2006.01) | |
| *B64F 5/00* | (2006.01) | |
| *B62D 55/265* | (2006.01) | |
| *B63B 59/10* | (2006.01) | |
| *G05D 1/02* | (2006.01) | |
| *B29C 53/58* | (2006.01) | |
| *B29C 70/38* | (2006.01) | |
| *B64B 1/58* | (2006.01) | |
| *G01N 21/90* | (2006.01) | |

(52) U.S. Cl.
CPC ............ *B64F 5/0045* (2013.01); *B62D 55/265* (2013.01); *B63B 59/10* (2013.01); *G05D 1/0227* (2013.01); *B29C 53/587* (2013.01); *B29C 70/382* (2013.01); *B64B 1/58* (2013.01); *G01N 21/9027* (2013.01); *G01N 21/9081* (2013.01)

USPC ............. 156/378; 156/64; 156/350; 156/358; 156/359; 156/360; 156/367; 156/379

(58) Field of Classification Search
CPC ..... B64F 5/0045; B62D 55/265; B63B 59/10; G05D 1/0227; B29C 53/587; B29C 70/382; B64B 1/58; G01N 21/9027; G01N 21/9081
USPC ........... 156/64, 350, 358, 359, 360, 367, 378, 156/379
See application file for complete search history.

(56) References Cited

U.S. PATENT DOCUMENTS

| | | |
|---|---|---|
| 6,397,131 B1 | 5/2002 | Busch et al. |
| 6,504,606 B2 | 1/2003 | Yagita |
| 7,690,596 B2 | 4/2010 | Eberle et al. |
| 7,997,532 B2 | 8/2011 | Tillotson |

(Continued)

FOREIGN PATENT DOCUMENTS

WO 2006085804 8/2006

*Primary Examiner* — Katarzyna Wyrozebski Lee
*Assistant Examiner* — Joshel Rivera
(74) *Attorney, Agent, or Firm* — McDermott Will & Emery LLP

(57) ABSTRACT

An airship hull repair system. The system includes a drive subsystem configured to move the system across an airship hull, a damage detecting subsystem configured to detect damage to the airship hull, a hull repair subsystem configured to repair the detected damage to the airship hull, and a magnetic coupling. The drive subsystem, the damage detecting subsystem, and the hull repair subsystem are included in an interior piece of the system configured to move on an interior of the airship hull and an exterior piece of the system configured to move on an exterior of the airship hull. The magnetic coupling couples the interior piece and the exterior piece to move together.

21 Claims, 3 Drawing Sheets

(56) References Cited

U.S. PATENT DOCUMENTS

| | | | |
|---|---|---|---|
| 2003/0048081 A1* | 3/2003 | Seemann | 318/68 |
| 2009/0166102 A1* | 7/2009 | Waibel et al. | 180/7.1 |
| 2010/0126403 A1 | 5/2010 | Rooney, III et al. | |
| 2010/0161095 A1 | 6/2010 | Lindgren | |
| 2011/0073708 A1 | 3/2011 | Biornstad et al. | |
| 2011/0127382 A1 | 6/2011 | Im | |
| 2011/0282536 A1 | 11/2011 | Rooney, III | |
| 2013/0126675 A1* | 5/2013 | Heppe | 244/126 |

\* cited by examiner

SELF-PROPELLED AIRSHIP HULL REPAIR SYSTEM

BACKGROUND

The present disclosure generally relates to a self-propelled airship hull repair system.

An airship's hull has the primary function of containing a lifting gas, which provides lift and enables vehicle operations. Holes and other damage can develop in the hull that allow lifting gas to escape. Such damage can develop both during hull manufacturing and airship operations.

The loss of lifting gas results in decreased hull lift and additional lifting gas resupply cost. Hulls are periodically inspected and repaired to ensure adequate lift. Traditional airship hulls are closely inspected either visually or with lift gas leak tools. Once a hole is discovered, maintenance personnel traditionally apply an external repair patch.

These traditional methods require the vehicle to be taken out of service for long periods of time due to the immense size of airship hulls. In addition, special equipment can be needed to access upper portions of the hull.

SUMMARY

According to one aspect of the present disclosure, an airship hull repair system is provided. The system includes a drive subsystem configure to move the system across an airship hull, a damage detecting subsystem configured to detect damage to the airship hull, a hull repair subsystem configured to repair the detected damage to the airship hull, and a magnetic coupling. The drive subsystem, the damage detecting subsystem, and the hull repair subsystem are included in an interior piece of the system configured to move on an interior of the airship hull and an exterior piece of the system configured to move on an exterior of the airship hull. The magnetic coupling couples the interior piece and the exterior piece to move together.

According to a further aspect of the present disclosure, a method of repairing an airship hull is provided. The method includes traversing the airship hull with an airship hull repair system including an interior piece configured to move on an interior of the airship hull and an exterior piece configured to move on an exterior of the airship hull, the interior piece magnetically coupled to the exterior piece, detecting, by the airship hull repair system, damage to the airship hull, and repairing, by the airship hull repair system, the detected damage.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

An airship's hull has the primary function of containing a lifting gas such as helium, which provides lift and enables vehicle operations. Holes and other damage can develop in the hull that allow lifting gas to escape. Such damage can develop both during hull manufacturing and airship operations.

The loss of lifting gas results in decreased hull lift and additional lifting gas resupply cost. Hulls are periodically inspected and repaired to ensure adequate lift. Traditional airship hulls are closely inspected either visually or with lift gas leak tools. Once a hole or other damage is discovered, maintenance personnel traditionally apply an external repair patch.

In some aspects, the present technology addresses the foregoing issues with a self-propelled airship hull repair system. The system includes a drive subsystem configure to move the system across an airship hull, a damage detecting subsystem configured to detect damage to the airship hull, a hull repair subsystem configured to repair the detected damage to the airship hull, and a magnetic coupling. The drive subsystem, the damage detecting subsystem, and the hull repair subsystem are included in an interior piece of the system configured to move on an interior of the airship hull and an exterior piece of the system configured to move on an exterior of the airship hull. The magnetic coupling couples the interior piece and the exterior piece to move together.

Figure 1:
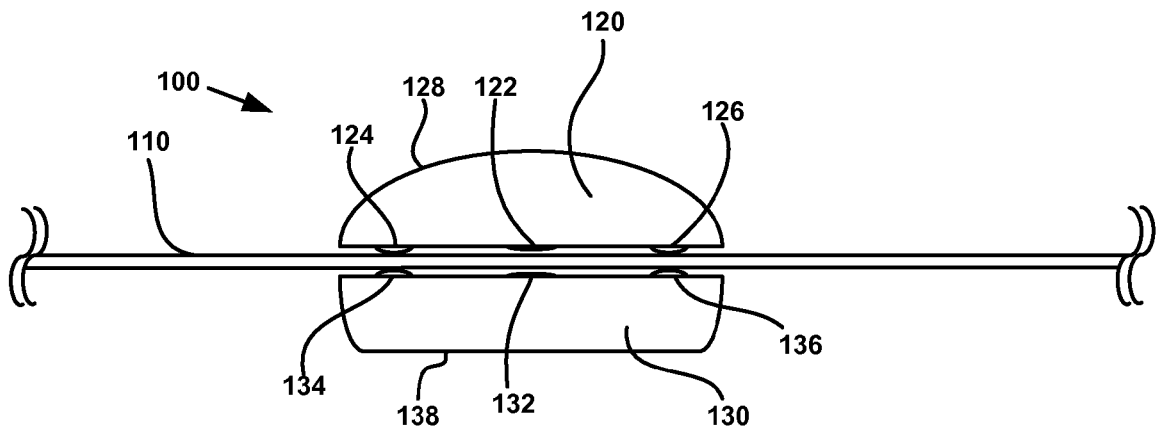
FIG. 1 illustrates an example of an airship hull repair system according to some aspects of the disclosure.

FIG. 1 illustrates an example of an airship hull repair system according to some aspects of the disclosure. Airship hull repair system 100 in FIG. 1 is configured to move across hull 110 of an airship such as a dirigible, blimp, hybrid airship, aerostat, or other lighter-than-air craft. The system includes exterior piece 120 configured to move on an exterior of hull 110 and interior piece 130 configured to move on an interior of hull 110. A magnetic coupling couples the exterior piece to the interior piece so that the pieces move together. This coupling is shown as magnetic couplings 122 and 132 in FIG. 1.

In some aspects, the magnetic coupling can include at least one magnet in each of exterior piece 120 and interior piece 130. In other aspects, the magnetic coupling can include at least one magnet in one of the pieces and a magnetically active material in the other one of the pieces. The magnets can be permanent magnets or electromagnets. Any other type of magnetic coupling can be used.

Each piece of hull repair system 100 includes a mechanism permitting motion across the airship hull. An example of this mechanism is illustrated as wheels 124 and 126 for exterior piece 120 and wheels 134 and 136 for interior piece 130. The disclosure is not limited to wheels. For example, rollers, tracks, balls, or any other type of mechanism that permits motion across hull 110 can be used.

The exterior piece and interior piece both include covers in FIG. 1. Exterior piece's cover 128 both protects exterior piece 120 and functions as an aerodynamic faring. Interior piece 130 is likewise protected by cover 138.

Figure 2:
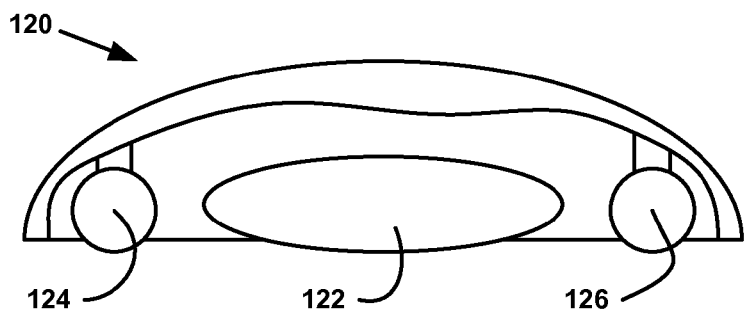
FIG. 2 illustrates a cut-away side view of an example exterior piece of an airship hull repair system according to some aspects of the disclosure.
Figure 3:
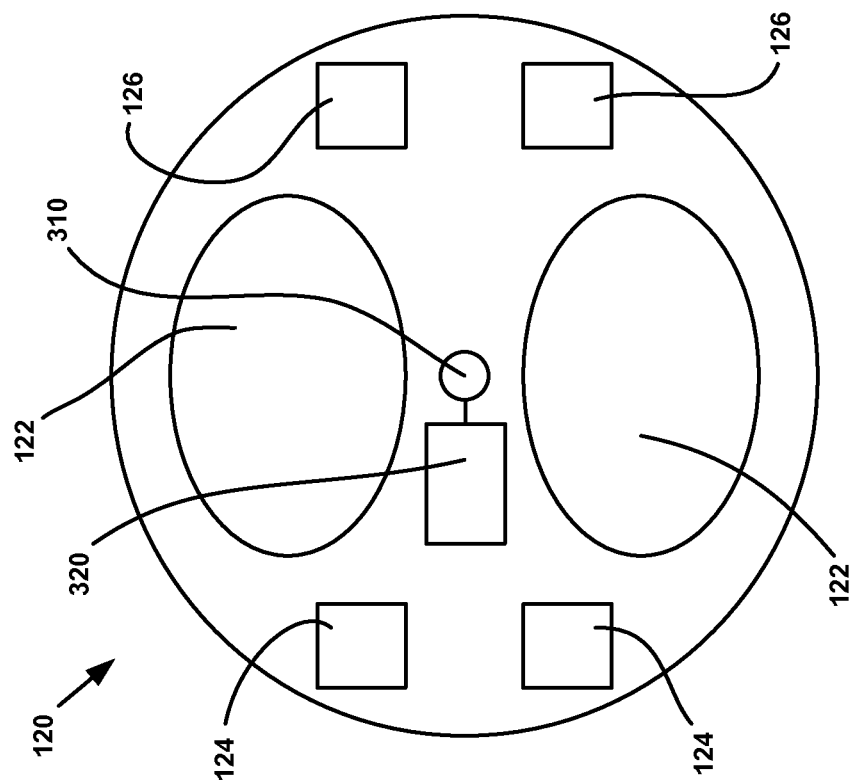
FIG. 3 illustrates a bottom view of an example exterior piece of an airship hull repair system according to some aspects of the disclosure.

FIG. 2 illustrates cut-away side view of an example exterior piece of an airship hull repair system according to some aspects of the disclosure, and FIG. 3 illustrates a bottom view of the example exterior piece. These views show a possible arrangement for magnetic coupling 122 and wheels 124 and 126. As shown in FIG. 3, magnetic coupling 122 can include multiple parts, and multiple wheels can be included. In other aspects, a different number of magnetic couplings and wheels can be included.

The example exterior piece 120 shown in FIG. 3 also includes light source 310 and power supply 320 for the light source. The light source can function as part of a damage detecting subsystem for airship hull repair system 100, as explained in more detail below.

Figure 4:
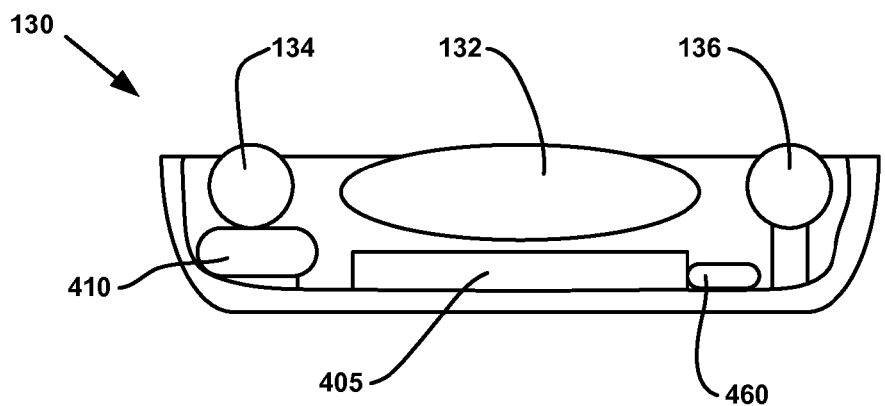
FIG. 4 illustrates a cut-away side view of an example interior piece of an airship hull repair system according to some aspects of the disclosure.
Figure 5:
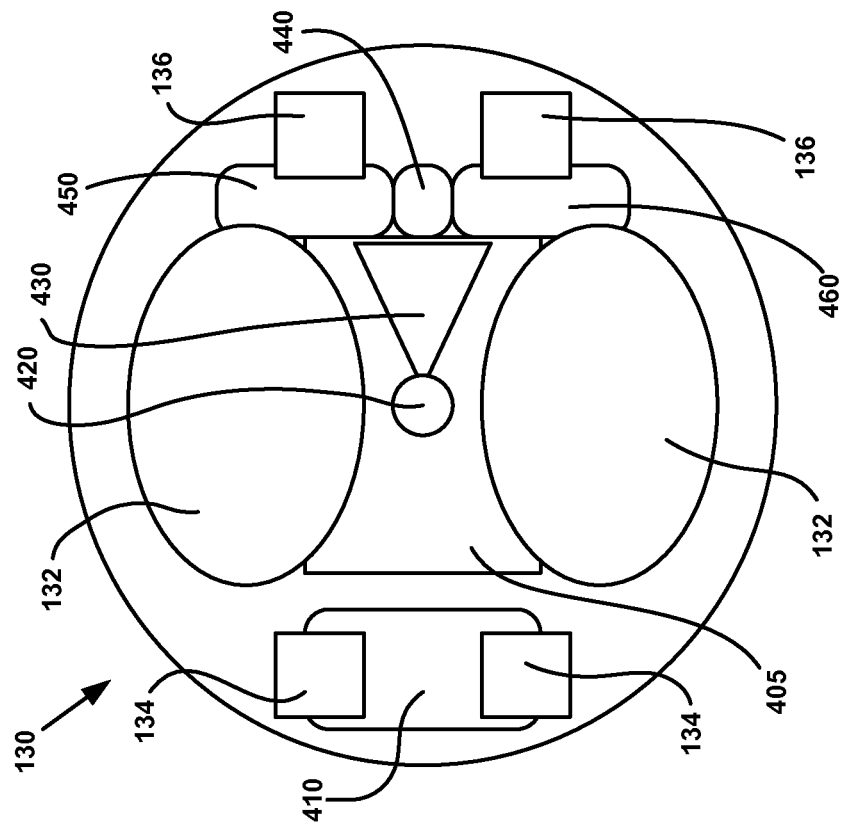
FIG. 5 illustrates a bottom view of an example interior piece of an airship hull repair system according to some aspects of the disclosure.

FIG. 4 illustrates a cut-away side view of an example interior piece of an airship hull repair system according to some aspects of the disclosure, and FIG. 5 illustrates a bottom view of the example interior piece. These views show a possible arrangement for magnetic coupling 132 and wheels 134 and 136. As shown in FIG. 5, magnetic coupling 132 can include multiple parts, and multiple wheels can be included. In other aspects, a different number of magnetic couplings and wheels can be included.

In some aspects, an arrangement of magnetic couplings in interior piece 130 matches an arrangement of magnetic couplings in exterior piece 120 in order to increase coupling through airship hull 110. An example of such an arrangement is shown in FIGS. 3 and 5. Other arrangements that provide sufficient magnetic coupling so that the exterior and interior pieces move together can be used.

The interior piece 130 shown in FIGS. 4 and 5 also includes power source 405, drive subsystem 410, part 420 of a damage detecting subsystem, hull repair subsystem 430, positioning subsystem 440, damage reporting subsystem 450, and control subsystem 460. In alternative aspects, fewer than all of these elements can be included, and additional elements can be included as well. Furthermore, the present technology is not limited to the particular layout of these elements shown in FIGS. 4 and 5.

Power source 405 provides power for the subsystems that require power. In addition, if the magnetic coupling of interior piece 130 includes one or more electromagnets, then power source 405 can provide power for those electromagnets.

Drive subsystem 410 is configured to move the airship hull repair system across an airship hull. The drive subsystem directly drives interior piece 130 across an interior of the hull. The movement of interior piece 130 in turn moves exterior piece 120 by virtue of the magnetic coupling between the pieces. In addition, this magnetic coupling allows the interior piece to move across the top and sides of the hull including while inverted. In other aspects, the drive subsystem can be included in exterior piece 120.

The drive subsystem also is configured to steer the airship hull repair system, for example by turning wheels 134. Thus, the airship hull repair system can be steered to avoid obstacles and to move over most if not all of the airship hull.

A part 420 of a damage detecting subsystem is shown as being included in interior piece 130 in FIGS. 4 and 5. The damage detecting subsystem is configured to detect damage to the airship hull when the airship hull repair system passes over or otherwise encounters the damage. Part 420 of the damage detecting subsystem included in the interior piece can take the form of a light sensor. The light sensor works in conjunction with light source 310 in exterior piece 120 to detect holes and other damage to airship hull 100. For example, a hole is detected when light from light source 310 shines through a hole to reach the light sensor.

In other aspects, the light source can be included in interior piece 130, and the light sensor can be included in exterior piece 120. In still other aspects, a different type of damage detecting subsystem can be used. For example, a damage detecting subsystem in the form of a gas detector can be included in exterior piece 120. Other types of damage detecting subsystems can be used.

Hull repair subsystem 430 included in interior piece 130 in FIGS. 4 and 5 is configured to repair the detected damage to the airship hull. Examples of hull repair subsystem 430 include but are not limited to an aerosol sealant dispenser and an adhesive patch applicator.

The interior piece 130 in FIGS. 4 & 5 also includes positioning subsystem 440 configured to determine a position of the airship hull repair system on an airship hull. For example, the positioning subsystem can include accelerometers that determine the airship hull repair system's location based on movement of the system. For another example, the positioning subsystem can include a transmitter and receiver, with the position of the system triangulated by an external locator system based on transmitted signals and then transmitted back to the positioning subsystem. For yet another example, the positioning subsystem can include a video camera that shows an area surrounding an airship hull repair system. Images from the video camera can be viewed by an operator to determine a position of the system. Any other form of positioning subsystem can be used, alone or in conjunction with some or all of these examples.

Damage reporting subsystem 450 of interior piece 130 is configured to report detected damage, for example to a bridge of an airship via wireless transmission. In other aspects, damage reporting subsystem 450 can store information about detected damage and then report that damage when the airship hull repair system returns to a base location in the airship for storage and maintenance. In certain aspects, damage reporting subsystem 450 can include cameras or the like for visually recording and then reporting detected damage and repairs.

Control subsystem 460 is provided to control the other subsystems of the airship hull repair system. For example, the control subsystem can control the drive subsystem to traverse an airship hull based on information from the positioning subsystem and to return to a base location for recharging and resupply. The control subsystem also can control the hull repair subsystem to repair hull damage based on information received from the damage detecting subsystem, and the control subsystem can control the damage reporting subsystem to report detected damage. Alternatively, the control subsystem can pass along instructions to the other subsystems from an external controller. The airship hull repair system can be controlled in other ways.

In some aspects, the control subsystem includes one or more processors and memory that stores instructions for the processor(s) to execute in order to control the airship hull repair system. In other aspects, the control subsystem includes specialized hardware for controlling the airship hull repair system. In still other aspects, the control subsystem can be implemented using any computing device, either local or remote, that is capable of controlling some or all of the subsystems of the airship hull repair system.

In some aspects, the airship hull repair system can be used when an airship is in flight. Such use can result in a risk that an exterior piece of the system could be blown off or otherwise lost. Aspects of the present technology address this risk by the division of subsystems between the exterior piece and the interior piece. In particular, the interior piece is at least somewhat protected by being inside the airship hull during flight and includes the bulk of the various subsystems. However, the present technology is not limited in this regard, and the subsystems can be divided between the exterior piece and the interior piece in any manner.

Figure 6:
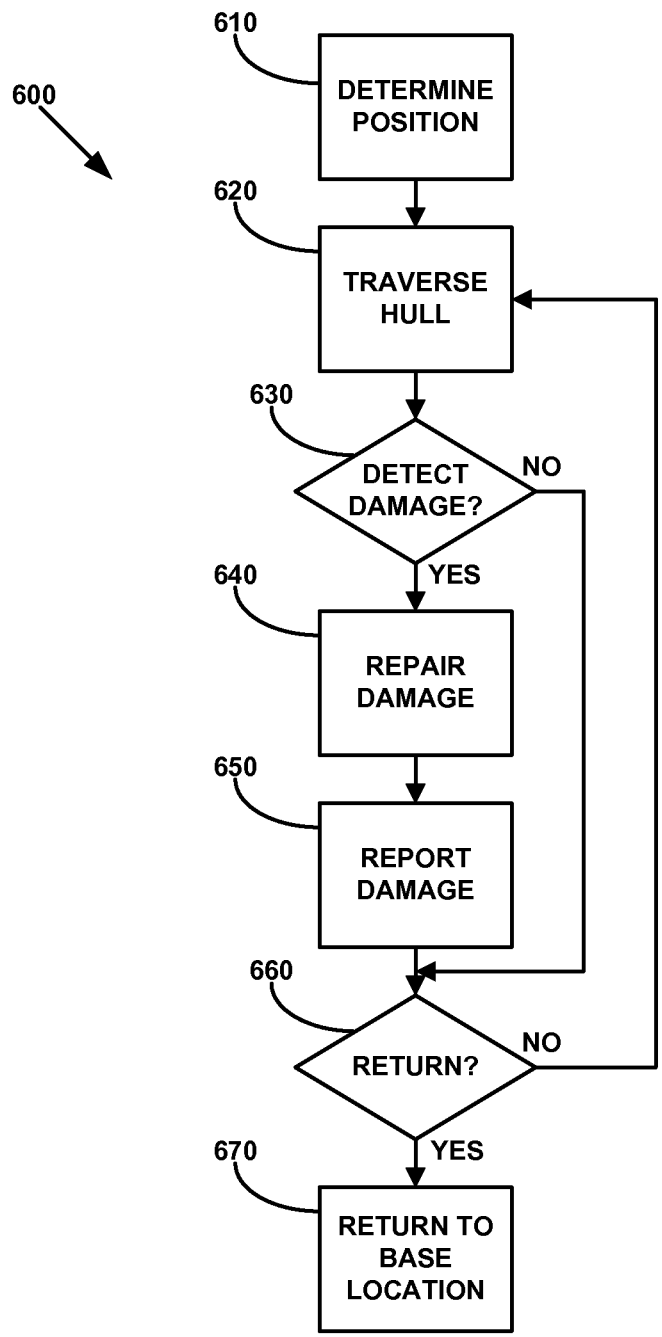
FIG. 6 illustrates an example method of repairing an airship hull according to some aspects of the disclosure.

FIG. 6 illustrates an example method of repairing an airship hull according to some aspects of the disclosure. A position of an airship hull repair system is determined in step 610. The position can be determined by the system or by an external computing device that controls the system. The determined position is used to control movement of the airship hull repair system to traverse an airship hull in step 620.

If damage such as a hole is detected on the airship hull in step 630, flow proceeds to steps 640 and 650 where the damage is repaired and reported, respectively. Steps 620 through 650 repeat until a time comes to return to a based location in step 660. An example of a base location is an enclosed bay accessible by the airship hull repair system and also by maintenance personnel for the airship.

An airship hull repair system according to aspects of the disclosure can be triggered to return to a base location, for example and without limitation, based on time, in response to an external control signal, and/or in response to a need to recharge power sources and/or resupply with hull repair materials. The airship hull repair system returns to a base location in step 670, for example for recharging, repair, and/or resupply.

In other aspects, an airship hull repair system can be used in ways different from those illustrated by the flowchart of FIG. 6. Furthermore, a phrase such as an "aspect" as used in this disclosure does not imply that such aspect is essential to the subject technology or that such aspect applies to all configurations of the subject technology. A disclosure relating to an aspect may apply to all configurations, or one or more configurations.

A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Likewise, while operations are depicted in the drawings in a particular order, this should not be understood as requiring that such operations be performed in the particular order shown or in sequential order, or that all illustrated operations be performed, to achieve desirable results. Moreover, the separation of various system components in the aspects described above should not be understood as requiring such separation in all aspects.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

These and other aspects of the subject technology are within the scope of the following claims.

What is claimed is:

1. An airship hull repair system, comprising:
   a drive subsystem configured to move the system across an airship hull;
   a damage detecting subsystem configured to detect damage to the airship hull;
   a hull repair subsystem configured to repair the detected damage to the airship hull; and
   a magnetic coupling;
   wherein each of the drive subsystem, a part of the damage detecting subsystem, and the hull repair subsystem comprises an interior piece of the system configured to move on an interior of the airship hull and an exterior piece of the system configured to move on an exterior of the airship hull; and
   wherein the magnetic coupling couples the interior piece and the exterior piece to move together.

2. The airship hull repair system of claim 1, wherein the damage detecting subsystem further comprises a light source included in the interior piece and a light sensor included in the exterior piece.

3. The airship hull repair system of claim 1, wherein the damage detecting subsystem further comprises a light source included in the exterior piece and a light sensor included in the interior piece.

4. The airship hull repair system of claim 1, wherein the damage detecting subsystem further comprises a gas detector included in the exterior piece.

5. The airship hull repair system of claim 1, wherein the hull repair subsystem further comprises an aerosol sealant dispenser.

6. The airship hull repair system of claim 1, wherein the hull repair subsystem further comprises an adhesive patch applicator.

7. The airship hull repair system of claim 1, wherein the magnetic coupling comprises at least one magnet in each of the interior piece and the exterior piece.

8. The airship hull repair system of claim 1, wherein the magnetic coupling comprises at least one magnet in the interior piece and a magnetically active material in the exterior piece, or at least one magnet in the exterior piece and a magnetically active material in the interior piece.

9. The airship hull repair system of claim 1, further comprising a control subsystem configured to control the drive subsystem, the damage detecting subsystem, and the hull repair subsystem.

10. The airship hull repair system of claim 1, wherein the exterior piece further includes a aerodynamic fairing.

11. The airship hull repair system of claim 1, further comprising a positioning subsystem configured to determine a position of the system.

12. The airship hull repair system of claim 1, further comprising a damage reporting subsystem configured to report the detected damage.

13. A method of repairing an airship hull, comprising:
traversing the airship hull with an airship hull repair system including an interior piece configured to move on an interior of the airship hull and an exterior piece configured to move on an exterior of the airship hull, the interior piece magnetically coupled to the exterior piece;
detecting, by the airship hull repair system, damage to the airship hull; and
repairing, by the airship hull repair system, the detected damage.

14. The method of claim 13, wherein detecting damage to the airship hull further comprises the airship hull repair system shining a light through the airship hull to a light sensor.

15. The method of claim 13, wherein detecting damage to the airship hull further comprises the airship hull repair system detecting a gas leaking to an exterior of the airship hull.

16. The method of claim 13, wherein repairing the detected damage further comprises dispensing an aerosol sealant onto the damage.

17. The method of claim 13, wherein repairing the detected damage further comprises applying an adhesive patch to the damage.

18. The method of claim 13, wherein the interior piece is coupled to the exterior piece with at least one magnet in each of the interior piece and the exterior piece.

19. The method of claim 13, wherein the interior piece is coupled to the exterior piece with at least one magnet in the interior piece and a magnetically active material in the exterior piece, or at least one magnet in the exterior piece and a magnetically active material in the interior piece.

20. The method of claim 13, further comprising reporting, by the airship hull repair system, the detected damage.

21. The method of claim 13, wherein the method is performed during flight of the airship.

* * * * *